United States Patent [19]

Tidemand

[11] Patent Number: 5,342,381

[45] Date of Patent: Aug. 30, 1994

[54] COMBINATION BIPOLAR SCISSORS AND FORCEPS INSTRUMENT

[75] Inventor: Kevin K. Tidemand, Maple Grove, Minn.

[73] Assignee: Everest Medical Corporation, Minneapolis, Minn.

[21] Appl. No.: 16,327

[22] Filed: Feb. 11, 1993

[51] Int. Cl.$^5$ ............................................. A61B 17/32
[52] U.S. Cl. ..................................... 606/174; 606/205; 606/52
[58] Field of Search .................... 606/51, 52, 174, 175, 606/205-211; 128/750-755

[56] References Cited

U.S. PATENT DOCUMENTS

| | | |
|---|---|---|
| 2,691,370 | 10/1954 | Wallace . |
| 3,651,811 | 3/1972 | Hildebrandt et al. . |
| 4,005,714 | 2/1977 | Hiltebrandt . |
| 4,248,231 | 3/1981 | Herczog et al. . |
| 4,862,890 | 9/1989 | Stasz et al. . |
| 5,026,370 | 6/1991 | Lottick . |
| 5,196,023 | 3/1993 | Martin ................................ 606/207 |

FOREIGN PATENT DOCUMENTS

| | | |
|---|---|---|
| 0517244 | 12/1992 | European Pat. Off. . |
| 0518230 | 12/1992 | European Pat. Off. . |
| 85002801 | 1/1985 | PCT Int'l Appl. . |

OTHER PUBLICATIONS

"Two New Laparoscopic Instruments: Bipolar Sterilizing Forceps and Uterine Manipulator" by Stephen Corson, Medical Instrumentation, vol. 11, No. 1.
Cameron-Miller product brochure for Model 80-7527.

*Primary Examiner*—Stephen C. Pellegrino
*Assistant Examiner*—William Lewis
*Attorney, Agent, or Firm*—Haugen and Nikolai

[57] ABSTRACT

A hand operable bipolar combination scissors and forceps instrument. The instrument comprises two interfacing blade members wherein at least one blade member is pivotable in relation to the other blade member and wherein each blade member is an electrode to which current can flow. Each blade member is shaped to cooperate with the other blade member to thereby form a distal forceps portion and a proximal scissors portion wherein the respective scissors portions are electrically insulated from each other along their interfacing surfaces. Preferably, each blade member is individually pivotable in relation to the other blade member, and the instrument is dimensioned to have utility in endoscopic or other similar procedures.

6 Claims, 3 Drawing Sheets

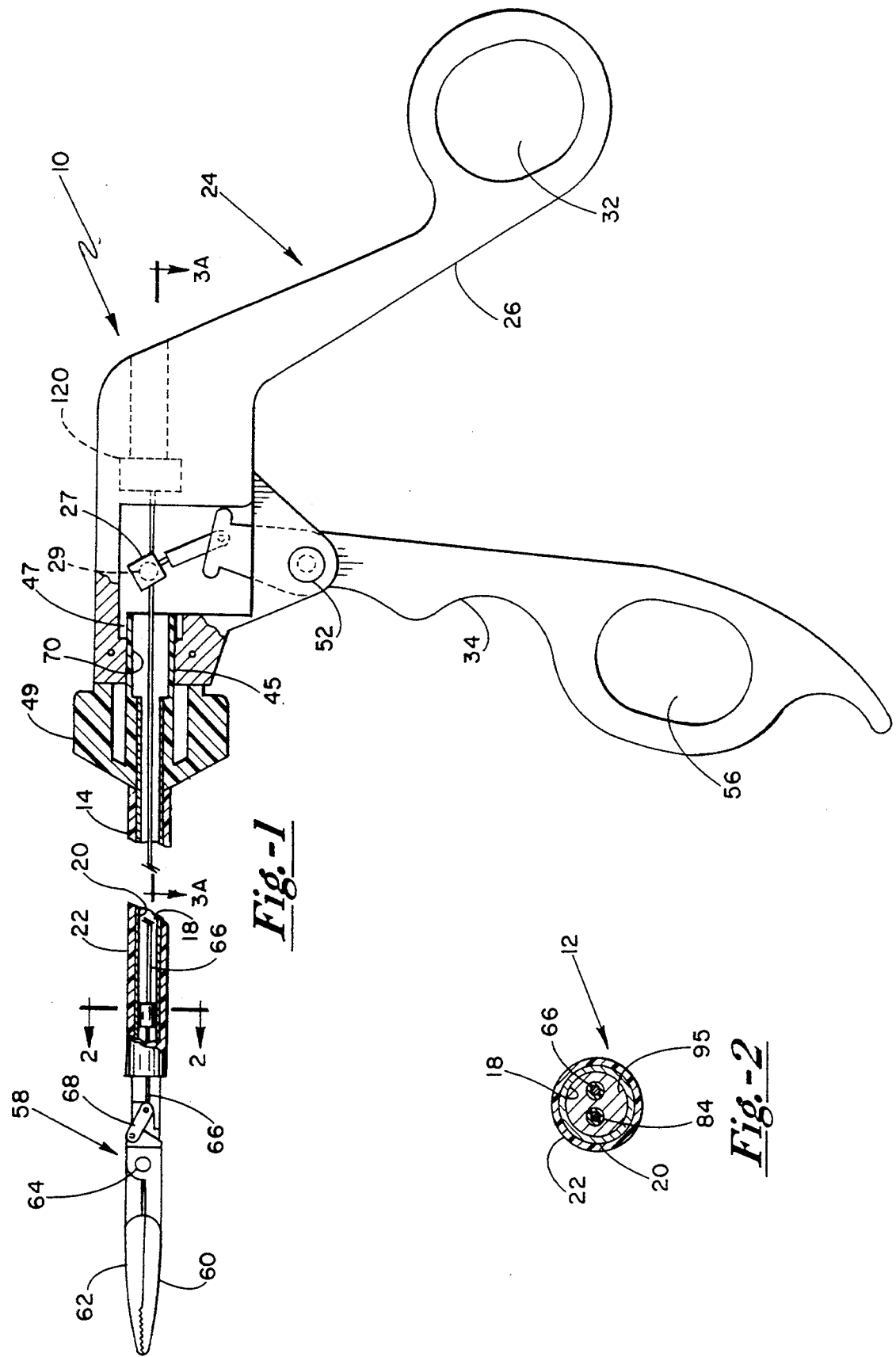

COMBINATION BIPOLAR SCISSORS AND FORCEPS INSTRUMENT

BACKGROUND OF THE INVENTION

I. Field of the Invention

This invention relates generally to surgical scissors and forceps, and in particular to a combination bipolar scissors and forceps instrument comprising two blade members which pivot in relation to each other and which are formed and cooperate with each other to provide an instrument having a forceps at its distal end and a scissors immediately proximal to the forceps. The forceps can be employed to grasp and cauterize tissue before or after cutting, while the scissors can provide cauterization during a cutting procedure.

II. Discussion of the Prior Art

Electrocauterization is a process whereby blood vessels (commonly called "bleeders") in tissue or alone which are cut during a surgical procedure are sealed closed by applying electrical energy at the site to, essentially, fuse by heat the vessel opening. In order to provide electrical energy at the site of bleeding, an instrument capable of conducting electricity must be placed at that site. The conductive instrument may be comprised of one electrode (monopolar) which cooperates with a remote conductive body plate electrode, or the instrument may be comprised of two closely spaced electrodes (bipolar). Current passing from one electrode to the other produces the heat sufficient to seal blood vessels or to coagulate blood and other fluids so coagulable. A bipolar instrument is generally preferred by a physician since current travel is over a short distance. A monopolar instrument usually requires electric current to travel a relatively long distance to the body plate electrode, with current directability and effect being unpredictable and possibly harmful to a patient.

Surgical scissors and surgical forceps individually are known in the art. Those available for use in endoscopically performed surgeries or other similar scope procedures are of a size to fit distally through the scope while having operating handles proximally of the scope. Generally, the scissors include a proximal scissors type handle, a central hollow tube through which a linkage from the handle passes, and a distal blade pair to which the linkage connects. Monopolar scissors, wherein both of the scissor blades form one pole and a remote body plate is the second pole, are available. Co-pending and commonly assigned Patent application Ser. No. 887,212, filed May 21, 1992 and incorporated herein by reference, teaches a bipolar scissors instrument where each blade thereof is a pole and wherein only one of the scissors blades pivots in relation to the other blade. A ceramic layer is present on each of the respective inner surfaces of each blade member, and insulation means at strategic sites throughout the instrument maintained bipolar capability for the separate blade members. Co-pending and commonly assigned U.S. Pat. application Ser. No. 08/013,869, filed Feb. 5, 1993, and entitled "Bipolar Electrosurgical Scissors," teaches a bipolar scissors instrument wherein both of the blades thereof pivot in relation to each other. Additionally, co-pending and commonly assigned U.S. Pat. application Ser. No. 08/013,852, filed Feb. 5, 1993, entitled "Bipolar Electrosurgical Forceps" teaches a bipolar forceps instrument with blades that pivot in relation to each other.

It is, of course, evident that a physician performing a procedure must presently change instruments if both bipolar scissors activity and bipolar forceps activity are desired. Because of this, it is a primary object of the present invention to provide a combination bipolar scissors and forceps instrument having two blade members which cooperate to function as both a scissors and a forceps.

It is a further object of the present invention to provide a combination bipolar scissors and forceps instrument usable in endoscopic or similar scope or cannular procedures.

Yet another object of the present invention is to provide a combination bipolar scissors and forceps instrument wherein operation thereof is achieved by a scissors type handle member.

These and other objects of the present invention will become apparent in the description of the invention which follows.

SUMMARY OF THE INVENTION

The present invention is a hand operable bipolar combination scissors and forceps instrument comprising two interfacing blade members wherein at least one blade member is pivotable in relation to the other blade member and wherein each blade member is an electrode to which current can flow, and further wherein each blade member is shaped to cooperate with the other blade member to thereby form a distal forceps portion and a proximal scissors portion. Each blade member comprises a substrate base upon which a layer of non-conductive material is secured on the surfaces of the scissors portion thereof which interface with a complimentrally shaped surface of the other blade member so that the non-conductive material of each blade member interfaces with that of the other at the meeting surfaces of the scissors portions along their entire lengths. The layer of non-conductive material must have adequate structural integrity to function as a shearing force. Preferably, the non-conductive layers are constructed of ceramic.

The blade members of the instrument are shaped such that their respective distal ends have substantially flat interfacing surfaces to thereby provide a forceps portion which performs to grasp or clamp tissue or vessel portions. Immediately proximal to the forceps portion, the blade members are shaped to provide a scissors portion such that respective interfacing surfaces meet in a manner to produce a shearing action as pivotal blade action occurs. In a preferred embodiment, pivotal movement of each blade member in relation to the other blade member is effectuated by two respective rigid rods, each coupled to a respective blade member, extending through a proximally disposed elongated tubular member having disposed at its proximal end a scissors type handle whose hand operation causes the blade members to pivot in relation to each other. Current is delivered to the blades through the rods which are connectable to an RF source and which are electrically insulated throughout the instrument. In this manner, a bipolar instrument having both grasping or clamping and cutting properties is provided for deployment to the site of a surgical procedure being performed endoscopically or similarly in a scope or cannula operating field.

BRIEF DESCRIPTION OF THE DRAWINGS

FIG. 1 is a side elevation view of a combination bipolar scissors and forceps instrument having two movable blade members, the drawing being partially sectioned to illustrate the working elements of the embodiment;

FIG. 2 is a cross-section view along line 2—2 of FIG. 1;

DETAILED DESCRIPTION OF A PREFERRED EMBODIMENT

Figure 3A:
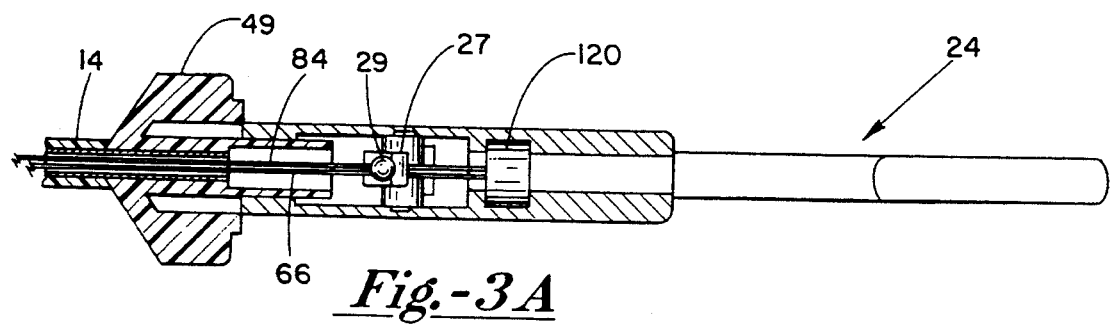
FIG. 3a is a partial top plan view of the proximal portion of FIG. 1.
Figure 3B:
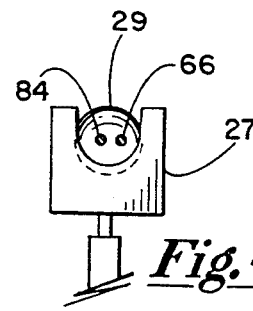
FIG. 3b is a front elevation view of a portion of a coupling for moving the two movable blades.

Referring to FIG. 1, a bipolar combination scissors and forceps instrument 10 is shown for use in endoscopic or similar procedures. The instrument 10 has an elongated tubular member 12 of a diameter and length sufficient for use in cooperation with a procedure performed using a scope type instrument. The tubular member 12 has a proximal end 14, a distal end 16 and a lumen 18 which extends for the entire length of the tubular member 12. As shown in the cross-sectional view of FIG. 2, the tubular member 12 comprises a metal tube 20 coated with an electrical insulator 22. The electrical insulator 22 is preferably a polymer such as Teflon ®. In addition to being an insulator, such a coating provides a lubricous surface which enhances its slidability through the lumen of an endoscope.

Disposed at the proximal end 14 of the tubular member 12 is a scissors type handle assembly 24. The handle assembly 24 has a first handle member 26 having first and second ends, with the first end thereof having a bore 30 extending therethrough and wherein, at the distal portion thereof, the proximal end 14 of the tubular member 12 resides. The first handle member 26 does not pivot. At its second end the first handle member 26 has a loop 32 intended to receive the thumb of an operator. The handle assembly 24 additionally has a second handle member 34 which is pivotal with respect to the first handle member 26 by being pivotally mounted to the first handle member 26 with a pivot pin 52. Pivotal movement is depicted by the broken line image shown in FIG. 1. The first end of the second handle member 34 has pivotally mounted thereto by pivot pin 23 and open top, U-shaped cradle member 27 in which is cradled a sphere 29 in indirect communication with the distal blade members as described later. Situated at the second end of the handle member 34 is a loop 56 to receive the forefinger of the operator.

Press fit into the distal end 16 of the tubular member 12 is a blade assembly 58. As will be explained more fully later, the blade assembly 58 comprises a first blade member 60 and a second blade member 62 pivotally joined to each other by an insulated rivet or screw 64 which extends through bores formed through the two blade members 60, 62. Both blade members 60, 62 are pivotally movable with respect to each other.

Figure 4:
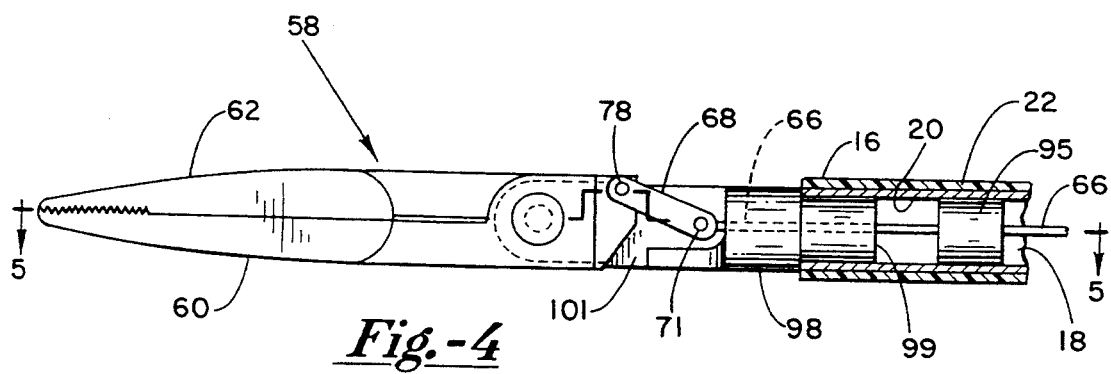
FIG. 4 is an enlarged side elevation view of the distal portion of FIG. 1.
Figure 5:
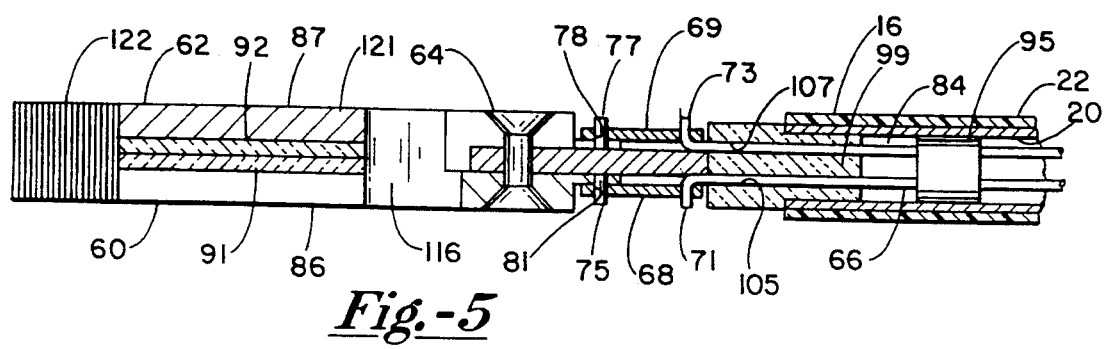
FIG. 5 is a cross-section view along line 5—5 of FIG. 4.

With reference to FIGS. 1 and 2, it is seen that two rigid electrically conductive rods 66, 84, each preferably covered with a layer of electrical insulation, extend through the lumen 18 of the tubular member 12. Referring to FIGS. 1, 4 and 5, which show the distal portion of the instrument 10, the rod 66, 84 are pivotally coupled to their respective blade members 60, 62 by respective rigid links 68, 69. The distal ends of the rods 66, 84 are turned laterally outwardly to fit through respective proximal pivot point openings 71, 73 of the links 68, 69 to thereafter form a rivet type connection. Situated at each of the proximal portions of the blade members 60, 62 in step-down sections thereof are laterally projecting posts 75, 77 which pass through distal pivot openings 78, 81 of the links 68, 69 do likewise form rivet type connections. The rigid lengths 68, 69 thereby can pivot at each of their respective proximal and distal end portions.

As is evident in FIGS. 4 and 5, the blade assembly 58 comprises, in addition to the blade members 60, 62, an insulated base 98 having a proximal portion 99 and a distal portion 101. The distal portion 101 has a bore 103 therethrough which provides a frame to which the blade members 60, 62 are pivotally attached via a pin or screw 64. The proximal portion 99 of the base 98 is press fit within the tubular member 12 and has two parallel longitudinal bores 105, 107 through which the rods 66, 84 pass. Proximal to the base 98 within the tubular member 12 is disposed and insulator member 95 through which the rods 66, 84 pass. This insulator member 95 functions to electrically isolate the rods 66, 84 from each other while mechanically acting to maintain them together. Their respective proximal ends of the rods 66, 84 extend proximally from the proximal end of the tubular member 12 through the sphere 29 and terminate in a free wheeling electrical connector 120. The free wheeling connector 120 cannot move translationally in the handle assembly 24, but can freely rotate. External leads originating from an electrosurgical generator (not shown) as known in the art provide current to the connector 120 to thereby provide current to the rods 66, 84.

Because the sphere 29 is freely rotatable within the cradle member 27, the tubular member 12, and therefore the blade members 60, 62 can be rotatably moved. A knob 49 is therefore provided near the proximal end of the tubular member 12 to facilitate easy rotation by hand of the blade members 60, 62 when blade member positioning is performed by the operator. As seen in FIG. 1, the rotatable knob 49 is generally cylindrical in shape, having a bore 70 through its center along the central axis. The bore 70 is large enough to accept the tube 20 therein and allow the conductive rods 66, 84 to pass therethrough. The proximal end of the tube 20 is frictionally inserted into the bore 70, to thereby rotate when the knob 49 is rotated. The knob 49 has an integrally formed tubular extension 45 which terminates in an annular flange 47. The handle assembly 24 has complimentrally shaped internal contours which accept the extension 45 and the flange 47 to thereby allow rotation thereof within the handle assembly 24. The knob 49 is preferably constructed of nylon so that the extension 45 and annular flange 47 will have lubricous characteristics for smoother rotation inside of the handle assembly 24. Because the rods 66, 84 are mechanically connected by the insulator member 95 which is stationary within the tube 20, rotation of the knob 49 results in rotation of the tube 20 as well as the rods 66, 84 to thereby also rotate the blade members 60, 62. Concurrently, the sphere 29 is rotated because the rods 66, 84 pass therethrough to their termination in the free wheeling electrical connector 120. As is evident from FIG. 1, operation of the handle assembly 24 by pivotally moving the second handle member 34 moves the cradle member 27 to thereby translationally move the sphere 29 which in turn moves both of the rods 66, 84 to thereby pivotally open and close the blade members 60, 62. In this manner, dual blade movement is accomplished. If only single blade movement is desired, the linkage arrangement described in copending and commonly-assigned U.S. Pat. application Ser. No. 887,212, filed May 21, 1992, entitled "Surgical Scissors With Bipolar Coagulation Feature" and incorporated herein by reference, can be employed. In that arrangement only one blade is in communication with and pivotable by moving the movable handle member of the handle assembly.

Referring to FIGS. 4–7, each blade member 60, 62 includes a metal blank 86, 87, preferably stainless steel, to which is bonded on the flat inner scissor surfaces which interface each other respective electrical insulators such as a ceramic sheet or layer 91, 92 of aluminum oxide or zirconia ceramic. Each blade member 60, 62 has a proximal scissors portion 121 and a distal forceps portion 122. Ceramic layers 91, 92 are each about 0.020 inch, and their working edges in the scissors portion 121 are beveled at an angle of about 45 degrees, thereby creating a gap of about 0.040 inch wide between the leading interfacing surfaces of the scissors portion 121 when the blade members 60, 62 are closed. An RF current applied to the blade members 60, 62 can cauterize tissue, vessels and the like which bridge this gap. To maintain the beveled edges of the ceramic layers 91, 92 in cutting contact, an integrally formed ramp surface 116 is provided to one side of the distal portion 101 of the base 98 to thereby effect one of the blade members, here shown being blade member 62. The ramp is achieved by appropriately molding or machining the insulated base 98 so as to leave a rise of approximately 0.005 inch, with the rise being in contact with the proximal portion of the blade member 62. When the blade members 60, 62 are affixed to each other, the blade member 62 is biased by the ramp surface 116, thereby forcing the ceramic layers 91, 92 of the scissors portion 121 against each other as the blade members 60, 62 are operated. The required shearing action is thereby maintained.

Figure 6:
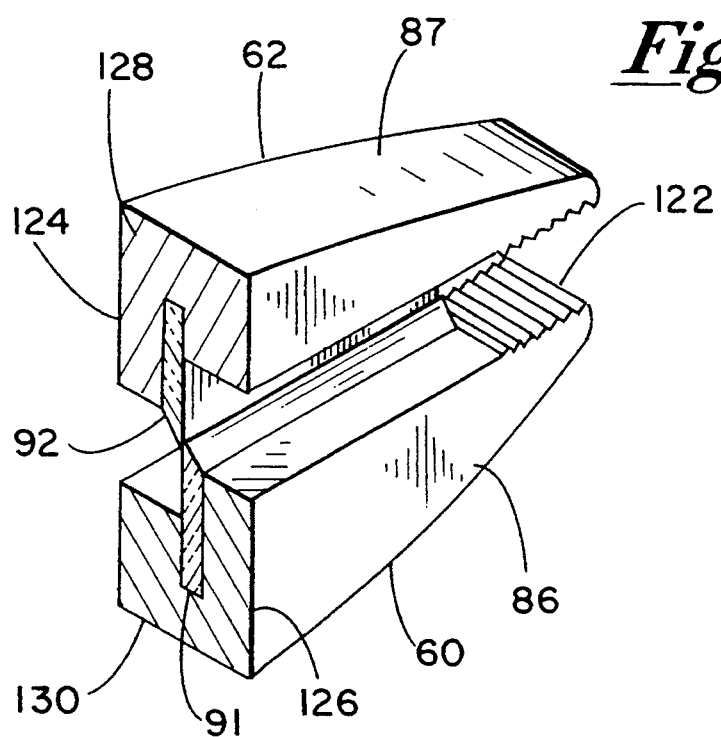
FIG. 6 is a perspective view of the blade members of FIG. 1.
Figure 7:
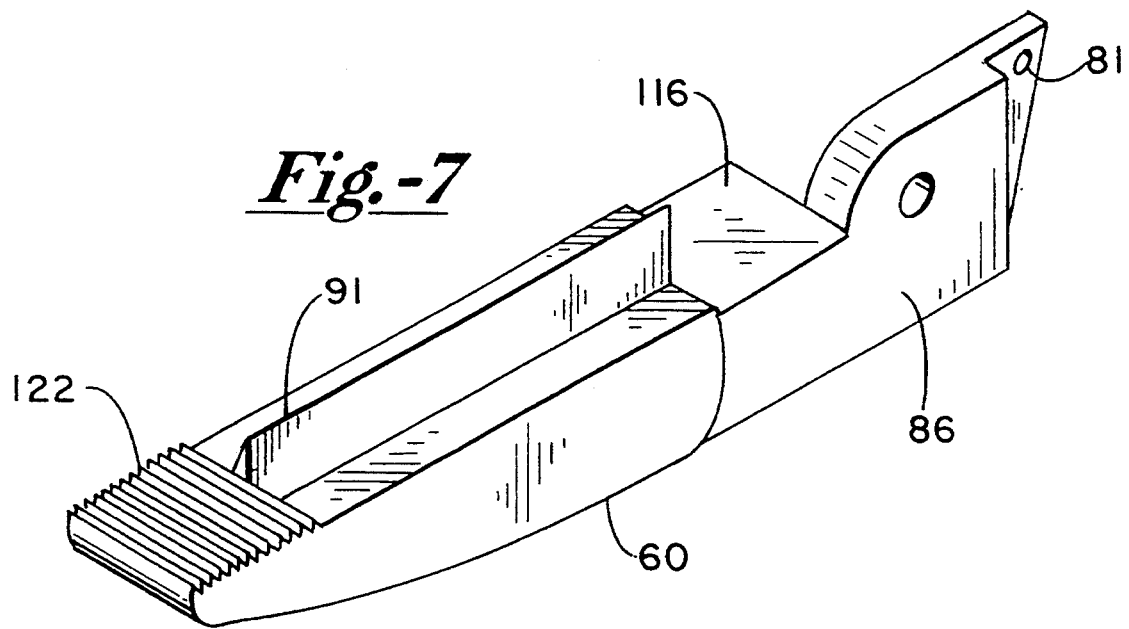
FIG. 7 is a perspective view of a single blade member of FIG. 6.

FIGS. 6 and 7 show in perspective the preferred blade member shape. In particular, FIG. 6 illustrates the blade members 60, 62 in a partially open configuration. As is there apparent, the metal blanks 86, 87 are uniformly tapered distally and have a constant width along their entire length. The proximal scissors portion 121 is formed by providing blanks 86, 87 having an L-shape or by respective vertical legs 124, 126 are juxtaposed such that respective horizontal legs 128, 130 are disposed at the free ends of the vertical legs 124, 126. Ceramic layers 91, 92 beveled at their meeting edges are bonded to the vertical legs 124, 126 to thereby provide shearing action upon blade movement- The distal ends of the metal blanks 86, 87 are flat to thereby form the forceps portion 122 of the blade members 60, 62. FIG. 7 shows the single blade member 60 wherein the forceps portion 122 is serrated to provide a better grasping action. The forceps portion 122 belonging to the other blade member 62 likewise can be complimentrally serrated for improved grasping action.

In operation, the physician or other care provider directs the distal portion of the instrument 10 through the endoscope or other similar device to thereby position the blade members 60, 62 at the site of treatment. Thereafter, with current supplied to the blade members, the handle member 24 is operated to cut or grasp tissue while simultaneously performing coagulation procedures.

While an illustrative and presently preferred embodiment of the invention has been described in detail herein, it is to be understood that the inventive concepts may be otherwise variously embodied and employed and that the appended claims are intended to be construed to include such variations except insofar as limited by the prior art.

What is claimed is:

1. A hand operable, bipolar, combination scissors and forceps instrument comprising two interfacing blade members wherein at least one blade member is pivotable in relation to the other blade member, and further wherein each blade member is shaped to cooperate with the other blade member to thereby form a distal forceps portion and a proximal scissors portion, each blade member being a metal electrode to which current can flow and having a ceramic insulator layer secured to the scissors portion thereof, whereby the ceramic insulator layer of one blade member interfaces with the ceramic insulator layer of the other blade member for electrically insulating one another along their entire lengths and wherein the interfacing ceramic layers each have a beveled cutting edge.

2. The instrument as claimed in claim 1 wherein each blade member is individually pivotable in relation to the other blade member.

3. The instrument as claimed in claim 1 wherein the metal is stainless steel.

4. A hand operable bipolar combination scissors and forceps instrument comprising:
   (a) an elongated tubular member having a proximal end, a distal end and a lumen extending therebetween;
   (b) two interfacing blade members disposed at the distal end of the tubular member and wherein at least one blade member is pivotable in relation to the other blade member, and further wherein each blade member is shaped to cooperate with the other blade member to thereby form a distal forceps portion and a proximal scissors portion, each blade member being a metal electrode to which current can flow and having a ceramic insulator layer secured to the scissors portion thereof whereby the ceramic insulator layer of one blade interfaces with the ceramic insulator layer of the other blade and wherein the interfacing ceramic layers each have a beveled cutting edge; and
   (c) a handle disposed at the proximal end of the tubular member, said handle being in communication with the blade members and being hand operable to thereby produce pivotal action of the blade members.

5. The instrument as claimed in claim 4 wherein each blade member is individually pivotable in relation to the other blade member.

6. The instrument as claimed in claim 4 wherein the metal is stainless steel.

* * * * *